United States Patent [19]
Acott et al.

[11] Patent Number: 5,985,830
[45] Date of Patent: Nov. 16, 1999

[54] USE OF IGF-I FOR THE TREATMENT OF KIDNEY DISORDERS

[75] Inventors: Philip D. Acott; John F. S. Crocker, both of Halifax, Canada

[73] Assignee: Dalhousie University, Halifax, Canada

[21] Appl. No.: 08/933,196

[22] Filed: Sep. 16, 1997

Related U.S. Application Data

[63] Continuation of application No. 08/710,331, Sep. 16, 1996, abandoned.

[51] Int. Cl.$^6$ .................................................. A61K 38/00
[52] U.S. Cl. ................................................................ 514/12
[58] Field of Search ................................................ 514/12

[56] References Cited

U.S. PATENT DOCUMENTS 5,565,428  10/1996  Clark et al. ................................ 514/12

*Primary Examiner*—Raymond Henley, III
*Attorney, Agent, or Firm*—Gray Cary Ware & Freidenrich; Stephen E. Reiter; June M. Learn

[57] ABSTRACT

In accordance with the present invention, there are provided methods for the treatment of polycystic kidney disease and related indications in mammals, employing IGF-I as the active agent. In accordance with another embodiment of the present invention, it has been discovered that IGF-I is an effective agent for the treatment of renal dysplasias and/or renal hypoplasias in mammals. In accordance with yet another embodiment of the present invention, it has been discovered that IGF-I is an effective agent for enhancing glomerular development in mammals. In accordance with still another embodiment of the present invention, it has been discovered that IGF-I is an effective agent for enhancing kidney development in mammals suffering from chronic organ injury.

24 Claims, 5 Drawing Sheets

USE OF IGF-I FOR THE TREATMENT OF KIDNEY DISORDERS

RELATED APPLICATIONS

This application is a continuation-in-part of U.S. Ser. No. 08/710,331, filed Sep. 16, 1996, now abandoned, incorporated by reference herein in its entirety.

FIELD OF THE INVENTION

The present invention relates to methods for the treatment of polycystic kidney disease in mammals. In another aspect, the present invention relates to methods for the treatment of renal dysplasias and/or renal hypoplasias in mammals. In yet another aspect, the present invention relates to methods to enhance glomerular development in mammals. In still another aspect, the present invention relates to methods to enhance kidney development in mammals suffering from chronic organ injury. In a further aspect, the present invention relates to methods to protect subjects from the ongoing toxicity of treatment with steroid hormones. In a still further aspect, the present invention relates to methods to maintain substantially normal growth in neonates and pre-pubescent mammals exposed to high dose steroid hormone therapy.

BACKGROUND OF THE INVENTION

Polycystic kidney disease is a heterogenous group of disorders characterized by large kidneys with epithelial lined cysts along the nephron collecting ducts of the affected kidneys. In all types of cystic kidney disease, the enlargement of the cyst wall is associated with hyperplasia of renal epithelium. There are several examples of genetic predisposition to cystic disease, with the most common forms of human polycystic kidney disease (PKD) being genetically transmitted as either an autosomal dominant trait or an autosomal recessive trait. There are also several forms of acquired polycystic kidney disease. Acquired lesions are caused by broad categories of agents, such as teratogens (e.g., diphenylamine and phthalates), agents affecting metanephric development (e.g., steroid hormones such as glucocorticoids), and as a consequence of loss of renal mass (as seen in end-stage renal disease). Even in kindreds with a defined genetic mutation, there is broad expression of the clinical phenotype. An example of this is a family with autosomal recessive PKD in several siblings, where the onset of renal failure was variable in the child and adolescent years. It is also well established that autosomal dominant PKD is asymptomatic in half of the kindred who are genetically affected, while approximately ⅙ go to renal failure. Moreover, the genetic trait does not discriminate the phenotypic variation of gender. The observation that the genetics are only one part of the clinical phenotype of PKD has created interest in looking at the pathophysiology of cystic disease and progression in the hope of finding modifying agents.

Currently, however, there is no effective treatment for Polycystic Kidney Disease (PKD), one of the three leading causes of end stage renal failure in humans (*Canadian Organ Replacement Register;* p. 95 [1990]). Although PKD simulates Mendelian inheritance, there is evidence that phenotypic expression of PKD involves genetic heterogeneity and multifactorial inheritance, including nongenetic factors.

The ready availability of non-invasive imaging techniques of ultrasound, computerized axial tomography and nuclear magnetic resonance imaging has confirmed that PKD is a common human ailment (Ogborn et al., *Pediatr. Res.,* 2: 123–146 [1988])). One in 1100 fetuses are affected and adult prevalence may be as high as 1 in 220. (Danovitch, In *Cystic Diseases of the Kidney,* Gardner, K D (ed), John Wiley & Sons Inc., Toronto, p. 125–150, (1975)); (Campbell, *Clin. Pediatr. Urol.,* Chapter 3: 181–186 (1951)). The probability of developing symptomatic renal insufficiency varies with age and pattern of presentation. It is known that both the number and size of cysts increase throughout life in this form of PKD, often starting in childhood. In the most common "adult" or dominantly inherited PKD (ADPKD), end-stage renal failure has been described in patients ranging from infancy (Taitz et al. *Arch. Dis. Child.,* 62: 45–49 [1987]) to the ninth decade (Churchill et al., *Kid. Int.,* 26: 190–193 [1984]). In this situation the cysts appear in the kidney in such large numbers that the renal parenchyma is destroyed thus contributing to end-stage renal failure.

The other major form of PKD is "infantile" or recessive PKD (ARPKD), which also has a wide range of clinical presentation (Zerres, *Pediatr. Nephrol.* 1: 397–404 (1987)). ARPKD can first be detected during the second trimester of pregnancy. Unfortunately, therapeutic abortion is the only prenatal intervention currently available.

The broad clinical spectrum of PKD suggests a complex interaction of genetic and other factors. Schimke has speculated that all forms of PKD may represent variable expression of common genes under different environmental influences (Schimke, *Problems in Diagnosis and Management of Polycystic Kidney Disease,* Grantham J J and Gardner K D (eds.) PKR Foundation, Kansas City, 49–69, (1985)). This concept is supported by much of the available experimental evidence. Wirth et al., (in *Hum. Genet,* 77: 221–222 (1987)), although not excluding such a concept, consider that family pedigrees and linkage studies confirm that ARPKD and ADPKD are mutations at distinct genetic loci, rather than being allelic mutations at the same locus.

Indeed, the locus of one gene marker of PKD, i.e., PKD1, has been mapped to chromosome 16 by Reeders et al. (*Nature,* 317:542–544 (1985)) and linked with biochemical polymorphisms and anonymous restriction fragment length polymorphism (RFLP) markers, thus permitting detection of asymptomatic individuals in the family (see also Reeders, *Pediatr. Nephrol.,* 1:405–410 (1987)). However, the gene(s) responsible for ADPKD in some families is/are not linked to the chromosome 16 locus (Kimberling et al., *NEJM,* 319 (14):913–918 (1988)). This genetic heterogeneity suggests that genetic screening must be approached with caution (Germino et al., *Am. J. Hum. Genet.,* 46:925–933 (1990)); Parfrey et al., *NEJM,* 323:1085–1090 (1990)).

In addition to the genetic heterogeneity of PKD, these traits show variable expressivity. The pathological features of the various forms of PKD exhibit overlaps, such as hepatic fibrosis, and distinguishing features, such as liver cysts in ADPKD. In addition, liver cystic disease may occur on its own without kidney cysts (Grunfeld et al., *Advances in Nephrology,* 14:1–20 (1985)). There is currently an inability to diagnose this disease either early in its progression or even at all. This situation is supported by the greater incidence of PKD seen at autopsy rather than in clinical practice.

The ethical and practical difficulties of studying induction of renal cysts in humans have encouraged the study of animal models. These models are well characterized in recent reviews (see, for example, Ogborn et al., *Pediatr. Res.,* supra; Brenner, *J. Am. Soc. Nephrol.,* 1:127–139

(1990); Avner et al., in: *The Cystic Kidney*. Eds. Gardner K D, Bernstein J, 55–98 (1990)). Reproducible models of PKD include those induced by organic chemicals—specifically diphenylamine, diphenylthiazole and nordihydroguaiaretic acid and those induced by the administration of glucocorticoids (Avner et al., supra) and (Perey et al., *Science*, 158: 494–496 (1967)).

Accordingly, there is still a need in the art for effective methods for the diagnosis and treatment of each of the various forms of polycystic kidney disease.

BRIEF DESCRIPTION OF THE INVENTION

In accordance with the present invention, we have discovered that IGF-I is an effective agent for the treatment of polycystic kidney disease and related indications in mammals. In accordance with another embodiment of the present invention, we have discovered that IGF-I is an effective agent for the treatment of renal dysplasias and/or renal hypoplasias in mammals. In accordance with yet another embodiment of the present invention, we have discovered that IGF-I is an effective agent for enhancing glomerular development in mammals. In accordance with still another embodiment of the present invention, we have discovered that IGF-I is an effective agent for enhancing kidney development in mammals suffering from chronic organ injury. In accordance with a further embodiment of the present invention, we have discovered that IGF-I is an effective agent for protecting kidneys from the ongoing toxicity of treatment with steroid hormones. In accordance with a still further embodiment of the present invention, we have discovered that IGF-I is an effective agent for maintaining substantially normal growth in neonates and pre-pubescent mammals exposed to high dose steroid hormone therapy.

BRIEF DESCRIPTION OF THE FIGURES

FIG. 3 illustrates the relative proportions of degrees of severity (histograms) of cystic disease, which is typically considered to be normally distributed and identically distributed as the severity of the disease.

DETAILED DESCRIPTION OF THE INVENTION

Figure 1:
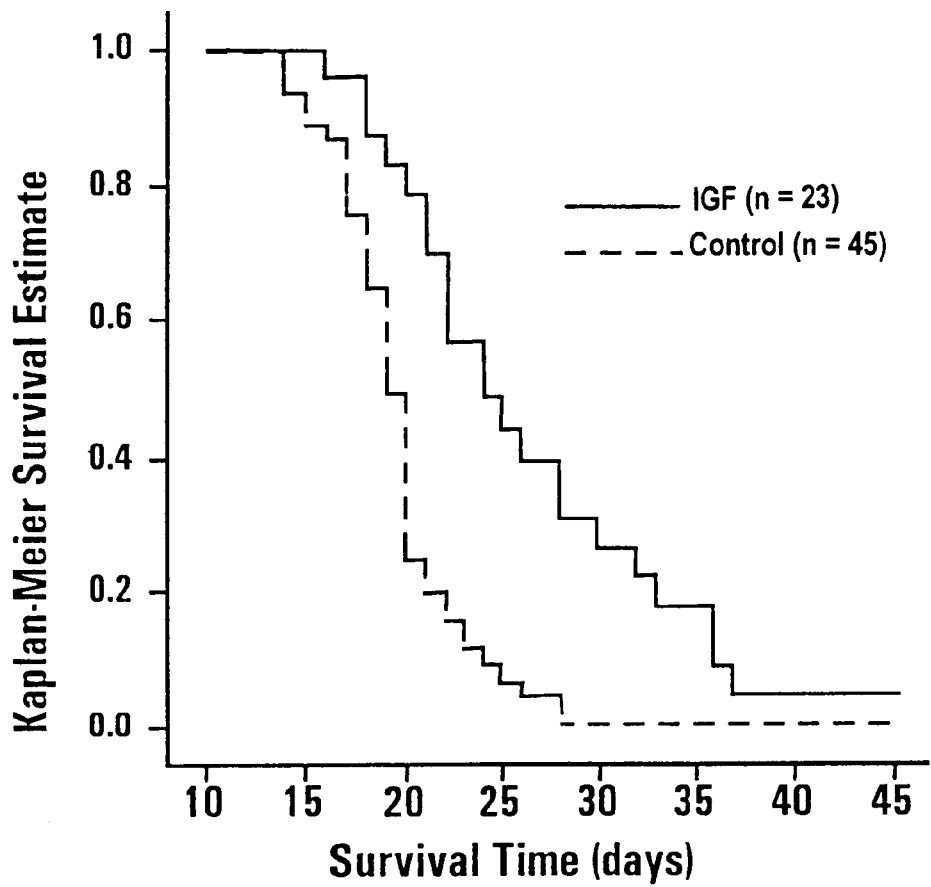
FIG. 1 presents plots of Kaplan-Meier survival estimates for cpk/cpk mice, demonstrating increased survival for mice given IGF-I for 24 consecutive days, starting on the second day of life. A log-rank test (Mantel-Cox) produced a $\chi^2$ statistic of 19.727, and a rank-sum test (Peto-Prentice) gave a $\chi^2$ statistic of 14.361, both with 1 df and both with p<0.0001. A Gill-Schumaker test demonstrated consistency with proportional hazards ($\chi=0.123$, 1 df, p=0.725).

In accordance with the present invention, there are provided methods for the treatment of polycystic kidney disease in a mammal. Invention methods comprise administering to a mammal in need thereof an effective amount of IGF-I.

As used herein, "mammal" signifies humans as well as other mammals, and includes animals of economic importance such as bovine, ovine, and porcine animals. The preferred mammal contemplated for treatment according to the invention is a human. Adults as well as non-adults (i.e., neo-nates, pre-pubescent mammals, and the like) are contemplated for treatment in accordance with the invention.

As described above, polycystic kidney disease is a heterogenous group of disorders characterized by large kidneys with epithelial lined cysts along the nephron collecting ducts of the affected kidneys. PKD can be the result of genetic predisposition (genetically transmitted as either an autosomal dominant trait or an autosomal recessive trait, or as the result of a spontaneous genetic mutation) or polycystic kidney disease can be acquired as a result of exposure to a variety of environmental factors.

Acquired lesions are induced by exposure to broad categories of agents, such as, for example, teratogens (e.g., amines such as diphenylamine, plasticizers such as phthalates, as well as derivatives thereof), agents affecting metanephric development (e.g., steroid hormones such as glucocorticoids), and as a consequence of loss of renal mass (as seen in end-stage renal disease).

IGF-I contemplated for use herein includes insulin-like growth factor-I from any species, including bovine, ovine, porcine, equine, and preferably human, in native-sequence or in variant form, and from any source, whether natural, synthetic, or recombinant. Also included within the scope of the present invention are analogs, homologs and mimics of IGF-I. Presently preferred herein for animal use is IGF-I from the particular species being treated, such as porcine IGF-I to treat pigs, ovine IGF-I to treat sheep, bovine IGF-I to treat cattle, etc. Similarly, presently preferred herein for human use is human native-sequence, mature IGF-I, more preferably without an N-terminal methionine, prepared, e.g., by the process described in EP 230,869 (published Aug. 5, 1987); EP 128,733 (published Dec. 19, 1984); or EP 288,451 (published Oct. 26, 1988). More preferably, this native-sequence IGF-I is recombinantly produced and is available from Genentech, Inc., South San Francisco, Calif., for clinical investigations.

Presently preferred IGF-I variants contemplated for use herein are those described in PCT WO 87/01038 (published Feb. 26, 1987) and in PCT WO 89/05822 (published Jun. 29, 1989), i.e., those wherein at least the glutamic acid residue at position 3 from the N-terminus of the mature molecule is absent, or those that have a deletion of up to five amino acids at the N-terminus. The presently most preferred variant has the first three amino acids from the N-terminus deleted (variously designated as brain IGF, tIGF-I, des(1-3)-IGF-I or des-IGF-I).

As used herein, reference to "analogs, homologs and mimics" of IGF-I embraces compounds which differ from the structure of native IGF-I by as little as the replacement and/or deletion of one or more residues thereof, to compounds which have no apparent structural similarity. Such compounds in all instances, however, have substantially the same activity as native IGF-I. Thus, "analogs" refers to compounds having the same basic structure as IGF-I, but differing in several residues; "homologs" refers to compounds which differ from native IGF-I by the deletion and/or replacement of a limited number of residues; and "mimics" refers to compounds which have no specific structural similarity with respect to IGF-I (indeed, a mimic need not even be a polypeptide), but such compound will display the biological activity characteristic of IGF-I and/or stimulate endogenous IGF-I production by the body.

As used herein, "treatment" refers to therapeutic and prophylactic treatment. Those in need of treatment include those already with the disorder as well as those in which treatment of the disorder has failed.

IGF-I employed in invention methods of treatment can be directly administered to the mammal by any suitable technique, including parenterally, intranasally, orally, transdermally, or by any other effective route. Examples of parenteral administration include subcutaneous, intramuscular, intravenous, intraarterial, and intraperitoneal administration. Most preferably, the administration is by continuous infusion (using, e.g., minipumps such as osmotic pumps), or by injection (using e.g., intravenous or subcutaneous means). It is presently preferred that the administration of IGF-I be accomplished by subcutaneous injection. Alternatively, IGF-I may also be administered as a single bolus, by slow-release or by depot formulation.

In addition, the IGF-I is appropriately administered together with any one or more of its binding proteins, for example, those currently known, i.e., IGFBP1, IGFBP2, IGFBP3 (which is described in U.S. Pat. No. 5,258,287 and by Martin and Baxter, 1986, J. Biol. Chem., 261: 8754–8760), IGFBP4, IGFBP5, or IGFBP6, or with the acid-labile subunit (ALS) of the IGF binding complex. Such proteins may be administered separately or as a complex with the IGF-I. The IGF-I may also be coupled to a receptor or antibody or antibody fragment for administration. In one embodiment of the invention, a preferred binding protein for IGF-I herein is IGFBP1.

It may be desirable to administer in conjunction with IGF-I other renally active molecules that promote reabsorption and retention of electrolytes such as, e.g., atrial natriuretic peptide (ANP), ANP analogs, or any variants thereof with or without receptor activity, urodilatin, human B-type natriuretic peptide (BNP), angiotensin receptor antagonist, vasopressin and its analogs, and endothelin antagonists such as antibodies or peptide antagonists. One example is BQ-123 (Ihara et al., Life Science, 50: 247–250 [1992]; JP 51-94254A published Aug. 3, 1993; Webb et al., Biochem. Biophys. Res. Comm., 185: 887–892 [1992]), a cyclic pentapeptide that is a potent and specific blocker of endothelin A receptors and blocks only the hypertrophic activity induced by endothelin-1, not CT-1, mouse LIF, or phenylephrine. Another example is the parent compound to BQ-123 described by Ihara et al., Biochim. Biophys. Res. Comm., 178: 132–137 (1991). Further examples include those described in EP 647,236; EP 647,449; EP 633,259 (phenylsulfonyl amino-pyrimidine derivatives); EP 601,386 (sulfonamide compounds); U.S. Pat. No. 5,292,740 (phenylsulfonamidopyrimidines); and U.S. Pat. No. 5,270,313 (phenyl-sulfonyl-aminopyrimidine derivatives). In addition, angiotensin-converting enzyme (ACE) inhibitors may be beneficial in conjunction with the IGF-I treatment of renal disorders.

The treatment regimen or pattern of administration of the agents may be one with simultaneous administration of a hyperglycemic agent (which counteracts the effects of IGF-I) and the IGF-I. In addition, the treatment regimen may be phasic with an alternating pattern of administration of one agent followed at a later time by the administration of the second agent. Phasic administration includes multiple administrations of one agent followed by multiple administrations of the second agent. The sequence that the agents are administered in and the lengths of each period of administration would be as deemed appropriate by the practitioner.

As a general proposition, the total pharmaceutically effective amount of IGF-I administered parenterally per dose will be an amount sufficient to provide a therapeutic effect without inducing a significant level of toxicity. Since individual subjects may present a wide variation in severity of symptoms and each form of IGF-I has its unique therapeutic characteristics, it is up to the practitioner to determine a subject's response to treatment and vary the dosages accordingly.

Typical dosages fall in the range of about 10 $\mu$g/kg/day up to about 200 $\mu$g/kg/day of patient body weight, although this is clearly subject to therapeutic discretion. If given continuously, the IGF-I is typically administered at a dose rate in the range of about 0.5 $\mu$g/kg/hour up to about 10 $\mu$g/kg/hour, either by 1–2 injections per day or by continuous subcutaneous release, for example, using a minipump, patch, implant, depot formulation, or the like.

IGF-I can also be suitably administered employing sustained-release systems. Suitable examples of sustained-release compositions include semi-permeable polymer matrices in the form of shaped articles, e.g. films, or microcapsules. Sustained-release matrices include polylactides (U.S. Pat. No. 3,773,919), copolymers of L-glutamic acid and gamma-ethyl-L-glutamate (Sidman et al., *Biopolymers*, 22:547–556 (1983)), poly (2-hydroxyethyl-methacrylate) (Langer et al., *J. Biomed. Mater. Res.*, 15:267–277 (1981)), ethylene vinyl acetate (Langer et al., supra) or poly-D-(–)-3 hydroxybutyric acid (EP133,988), and the like.

Sustained-release IGF-I compositions also include liposomally entrapped IGF-I. Liposomes are prepared by methods known in the art (see, for example, DE3,218,121; U.S. Pat. Nos. 4,485,045 and 4,545,545). Ordinarily, liposomes are of small (about 200–800 Angstroms) unilamellar type in which the lipid content is greater than about 30 mol. % cholesterol, the selected proportion being adjusted for the optimal IGF-I therapy.

For parenteral administration, in one embodiment, IGF-I is formulated by mixing in a unit dosage injectable form (solution, suspension, or emulsion), with a pharmaceutically acceptable carrier, i.e., one that is non-toxic to recipients at the dosages and concentrations employed and is compatible with other ingredients of the formulation. The formulation preferably does not include oxidizing agents and other compounds that are known to be deleterious to polypeptides.

Generally, the formulations are prepared by contacting the IGF-I uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples include water, saline, Ringers solution, dextrose solution, and the like. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as poly-vinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxmers, or PEG. The IGF-I is typically formulated in such vehicles at a concentration of about 0.1 mg/ml to 100 mg/ml, preferably 1–10 mg/ml, at a pH of about 3 to 8. For example, full length IGF-I is generally stable at a pH of no more than about 6, while des(1-3)-IGF-I is stable at about 3.2 to 5. It will be understood that use of certain of the foregoing excipients, carriers, or stabilizers will result in the formation of IGF-I salts.

In addition, the IGF-I, preferably full-length IGF-I, is suitably formulated in an acceptable carrier vehicle to form a pharmaceutical composition, preferably one that does not contain cells. In one embodiment, the buffer used for formulation will depend on whether the composition will be employed immediately upon mixing or stored for later use. If employed immediately, full length IGF-I can be formulated in mannitol, glycine, and phosphate at pH 7.4. If this mixture is to be stored, it is preferably formulated in a buffer at a pH of about 6, in the optional further presence of a surfactant that increases the solubility of the IGF-I at this pH. Examples of such surfactants are 0.1% polysorbate 20 or poloxamer 188. The final preparation may be a stable liquid or a lyophilized solid.

IGF-I to be used for therapeutic use must be sterile. Sterility is readily accomplished by filtration through sterile filtration membranes (e.g. 0.2 micron membranes). Therapeutic IGF-I compositions generally are placed into a container having a sterile access port, for example, a vial having a stopper pierceable by a hypodermic injection needle.

IGF-I ordinarily will be stored in unit or multi-dose containers, for example, sealed ampoules or vials, as an aqueous solution, or as a lyophilized formulation for reconstitution. As an example of a lyophilized formulation, 10-ml vials are filled with 5 ml of sterile-filtered 1% (w/v) aqueous IGF-I solution, and the resulting mixture is lyophilized. The infusion solution is prepared by reconstituting the lyophilized IGF-I in bacteriostatic Water-for-Injection.

While the IGF-I can be formulated in any way suitable for administration, the preferred formulation contains about 2–20 mg/mL of IGF-I, about 2–50 mg/mL of an osmolyte, about 1–15 mg/mL of a stabilizer, and a buffered solution at about pH 5–6, more preferably pH about 5–5.5. Preferably, the osmolyte is an inorganic salt at a concentration of about 2–10 mg/mL or a sugar alcohol at a concentration of about 40–50 mg/mL, the stabilizer is benzyl alcohol or phenol, or both, and the buffered solution is an acetic acid salt buffered solution. More preferably, the osmolyte is sodium chloride and the acetic acid salt is sodium acetate. Even more preferably, the amount of IGF-I is about 8–12 mg/mL, the amount of sodium chloride is about 5–6 mg/mL, the amount of benzyl alcohol is about 8–10 mg/mL, the amount of phenol is about 2–3 mg/mL, and the amount of sodium acetate is about 50 mM so that the pH is about 5.4. Additionally, the formulation can contain about 1–5 mg/mL of a surfactant, preferably polysorbate or poloxamer, in an amount of about 1–3 mg/mL. Alternatively, the formulation is suitably IGF-I dissolved at 5 mg/ml in 10 mM citrate buffer and 126 mM NaCl at pH 6.

In accordance with another embodiment of the present invention, there are provided methods for the treatment of renal insufficiencies in mammals, said method comprising administering an effective amount of IGF-1 to said mammal.

Patients who present renal insufficiencies include those with renal dysplasias, renal hypoplasias, congenital renal anomalies, acute renal failure, and the like. Invention treatment is particularly beneficial, as it has been discovered to promote improved growth of the subject being treated (of particular importance where the subject is not an adult). In addition, invention treatment has also been discovered to minimize catabolism by the subject being treated (which can aid in minimizing the weight loss which can frequently accompany the occurrence of renal insufficiencies.

In accordance with yet another embodiment of the present invention, there are provided methods to enhance glomerular development in mammals, said method comprising administering an effective amount of IGF-I to a mammal in need thereof.

Patients for whom enhanced glomerular development is indicated include patients with renal hypoplasia, renal dysplasia, spinal bifida, solitary kidneys, interuterine growth retardation, pediatric syndromes with growth anomalies (e.g., Turner's Syndrome and Down's Syndrome), and the like.

In accordance with still another embodiment of the present invention, there are provided methods to enhance kidney development in mammals suffering from chronic organ injury, said method comprising administering an effective amount of IGF-I to said mammal.

Patients for whom enhanced kidney development is indicated include adults who have undergone transplantation of a small kidney (wherein further growth of the organ is ablated), subjects who suffer from renal tubule poisoning, subjects who have undergone chemotherapy (e.g., cancer patients), and the like.

In accordance with a further embodiment of the present invention, there are provided methods to protect subjects from the ongoing toxicity of treatment with steroid hormones, said method comprising administering an effective amount of IGF-I to a subject undergoing treatment with steroid hormones.

Patients for whom protection from the ongoing toxicity related to treatment with steroid hormones is indicated are patients suffering from any disease which is commonly treated by the administration of steroids, such as, for example, renal disorders (e.g., post renal transplant, primary and secondary glomerularnephritis, and the like), nephrotic syndrome, collagen vascular diseases, various forms of arthritis (e.g., rheumatoid arthritis, and the like), inflammatory bowel disease, asthma, and the like. As readily recognized by those of skill in the art, administration of IGF-1 in conjunction with the administration of steroids can be carried out in a variety of ways, e.g., in combination with the steroid, as a separate administration at about the same time as the steroid is being administered, or some time prior to or after administration of the steroid.

In accordance with another embodiment of the present invention, there are provided methods to maintain substantially normal growth in neonates and pre-pubescent mammals exposed to high dose steroid hormone therapy, said method comprising administering an effective amount of IGF-I to said mammal.

Patients for whom maintenance of substantially normal growth is desired are neonates and pre-pubescent mammals exposed to high dose steroid hormone therapy, which is used to treat a variety of indications, e.g., bronchopulmonary dysplasia in premature infants, nephrotic syndrome in children, collagen disorder, rheumatoid arthritis, total villous atrophy, and the like.

The invention will now be described in greater detail by reference to the following non-limiting examples.

EXAMPLES

The laboratory mouse as an experimental model is well characterized in PKD (ogborn et al., *Pediatr. Res.,* supra; Brenner, supra; Avner et al., supra). The murine model is universally utilized for a variety of reasons, e.g., because the genetics of inbred strains are well defined (Charlton, *Quarterly J. Exp. Physiol.,* 69:655–676 (1984); In *Handbook on Genetically Standardized Jax Mice,* 3rd edition, Eds Heiniger and Dorey, The Jackson Laboratory; and *Genetic Variants and Strains of Laboratory Mouse,* 2nd edition, Eds Lyon and Searle, Oxford University Press). Moreover, patterns of mouse susceptibility to GC-induced PKD have been extensively examined. Furthermore, there are established Mendelian mutations resulting in PKD (Preminger et al., *J. Urol.,* 127: 556–560 [1982]), most notably the recessive cpk mutation, now localized to mouse chromosome 12 (Davisson et al., *Genomics,* 9: 778–781 [1991]).

Histological and biochemical characterization of the cpk mutation has been extensively studied (Crocker, et al., *Kidney Int.,* 31: 1088–1091 [1987]); Cowley et al., *Proc. Natl. Acad. Sci. U.S.A.,* 84: 8394–8398 [1987]); (Ebihara et al., *Lab. Invest.,* 58(3): 262–269 [1988]) and Avner et al., *Kidney Int.,* 36: 960–968 [1989]). The presence of hepatic cysts in heterozygous (cpk/+) animals have been described (Grimm et al., *J. Exp. Path.,* 71: 119–131 [1990]). Indeed, there is strong evidence that both glucocorticoids and thyroid hormone are involved in the expression of the cpk/cpk mutation. This includes the increased levels of corticosteroids in mutants early in life and serum lipid and thyroid hormone profiles of mutants, consistent with hypothyroidism (Crocker et al., *Teratoloqy,* 43: 571–574 [1991]). It has also been observed that transgenic mice constitutively expressing the c-myc gene product (as a result of a SV40 promotor insert) are characterized by PKD (Trudel et al., *Kidney Int.,* 39: 665–671 [1991]), thus providing a valuable window on an early step in the pathophysiology of PKD.

Another model that may be used to study the progression of PKD is to administer large doses of glucocorticoids (GC) to newborn animals. This has been shown to induce PKD in rabbits (Baxter, *Brit. J. Exp. Path.,* XLI:140–149 (1960)), rats (Perey et al., supra), hamsters (Filmer et al., *Am. J. Path.,* 72(3):461–468 (1973)), and mice (Crocker et al., In *Abnormal Functional Development of the Heart, Lungs and Kidneys,* Eds. Kavlock and Grabowski, Liss, New York, p. 281–296 (1983)). As in the human disease, these cysts are lined by functioning tubular epithelium (Ojeda et al., Nephron., 42:240–248 [1986]). Hormonal manipulation, particularly with corticosteroids, increases glomerular filtration rates (Baylis et al., *Am. J. Physiol.* 248:F166-F170 1978)), enlarges the area of tubular basolateral membranes (TBM) (Wade et al., *J. Cell Biol.* 81:439–445 [1979]) and influences a wide range of transmembrane transport processes both on the luminal and basolateral surfaces of the tubular epithlium.

Crocker et al., supra. have established that acetate salts of GC were the most effective in inducing PKD and that such induction was independent of any hypokalemia that therapy might induce (Crocker et al., *Am. J. Path.,* 82: 373–380 [1976]). They then sought to explore the site of action of GC's by simultaneous treatment with agents opposing their electrolyte transport effects (Crocker et al., *Clin. Invest. Med.,* 11(1):16–21 [1988]). They established that lithium chloride enhances cyst formation despite its natriuretic effects. Thus it is possible that both lithium and GC may modulate a pathway of tubular proliferation that is independent of electrolyte transport.

During the course of the present studies, carried out in randomly inbred Sprague-Dawley rats, the possibility was considered that experiment-to-experiment differences might arise, in part, from divergence in various lines obtained from different suppliers. This hypothesis was tested by studying GC-induction potential in the mouse, using 18 well-characterized inbred strains. All strains tested were found to be susceptible to PKD induction. The proportion of cystic change at a specific dose (250 mg/kg) and the spectrum of PKD severity was found to vary among strains in a manner best predicted by a multifactorial model with its continuous, normally distributed function of liability (i.e. susceptibility) (McDonald et al., *Kidney Int.,* 37:901–908 [1990]). The C57B1/6J strain, the original background strain for the cpk mutation, has virtually the lowest threshold and, therefore, the highest proportion of affected animals. Other background strains, notably the DBA/2J have significantly less susceptibility, while the B10.M-H-2 congenic inbred strain was highly resistant.

Glucocorticoids also produce cysts in murine embryonic organ culture (Avner et al., *Experientia,* 40: 489–490 [1984]), in the presence and absence of serum components. Avner et al., supra. have shown that this phenomenon correlates with Na±K+ATPase activity, and can be reduced by treatment with ouabain (Avner et al., *Kidney Int.,* 28: 447–455 [1985]). Modification in the culture media of thyroid hormone levels, a potent inducer of the enzyme, also modified cyst production (Avner et al., *J. Lab. Clin. Med.,* 109: 441–453 [1987]). There is evidence that the cellular distribution of the enzyme is abnormal in the organ culture model of PKD. Preliminary data suggest that C3H mice (a very susceptible strain) have a blunted response to induction of this ATPase by methylprednisolone acetate (MPA) compared to the relatively resistant DBA/2J strain, despite similar cytoplasmic receptor status (Ogborn et al., *Pediatr. Res.,* 27: 335A [1990]) and (Ogborn et al., *Kidney Int.,* 37: 425 19901). This is the reverse of what might be predicted from the in vitro work. As this enzyme is the source of the electrochemical gradient responsible for tubular transport of many solutes, induction of this enzyme would favour greater tubular transport of many solutes, induction of this enzyme would favour greater tubular egress of fluid and electrolytes in resistant animals, an effect that would oppose cyst growth. This can now be explained by change of location of Na+K+-ATPase in the tubular cell.

The cpk mutation model for PKD was first described in detail by Preminger et al., supra. Homozygous mutants (cpk/cpk) develop renal enlargement a few days after birth which are generally palpable at 10 to 14 days. Homozygous cpk mice have elevated plasma corticosterone levels early in postnatal life when adrenal corticosterone production is usually suppressed and unresponsive to physiologic stimuli (Crocker et al., *Kidney Int.,* supra). The homozygous mutants die within the first month of life.

Histologically, the cystic changes are characterized by early proximal tubular changes in late gestation (Nidess et al., *J. Urol.,* 131: 156–162 [1984]), and in organ explant are associated with increase sodium potassium AtPase activity (Avner et al.. *Kidney Int.,* supra). These dilatations regress after birth as the severe terminal change of the distal nephron commences. These lesions bear strong resemblance pathologically to the glucocorticoid induced PKD which is seen in the C57B1/6J mouse. The cpk mutation was first noted in the C57B1/6J background.

The evolution of PKD in cpk homozygotes is associated with increased expression of the c-myc proto-oncogene; however, the specificity of this response in the cpk model and its relation to cystogenic changes in cpk homozygote have not been addressed (Cowley et al., supra). In other tissues, this gene has been shown to be susceptible to glucocorticoid modulation (Forsthoefel et al., *Molec. Endocrin.,* 1(12): 899–907 [1987]) which further implicates a central role to a glucocorticoid abnormality in PKD.

Cystic liver disease has been noted in 50% of cpk heterozygous mice by one year of age, making it pathologically similar to ADPKD, where 40% of patients show cystic liver disease. This makes the cpk mutant mouse model appear analogous to ADPKD rather than ARPKD, where hepatic fibrosis is seen uniformly (Grimm et al., supra). The homozygote cpk/cpk mice die by three to four weeks of age and thus one cannot tell whether cystic liver disease might develop in this subgroup.

Retinoic acid is a molecule belonging to the chemical class known as retinoids. In vivo, the retinoid exists as retinol, retinal, and all-trans-retinoic acid (RA). Retinol and retinoic acid are essential in the control of epithelial growth and cellular differentiation and have important effects on embryonic development.

Embryonic developmental organogenesis is dependent upon growth, differentiation, pattern formation, and morphogenesis. Each of these processes is dependent upon inductive interactions between cells. Humes et al.,*Exp. Cell Res.,* 201:8–15 (1992) worked with primary cultures of rabbit renal proximal tubule cells in hormonally defined, serum-free media treated with transforming growth factor-beta 1 (TGF-beta 1), epidermal growth factor (EGF), and all trans-retinoid acid singly or in combination. It was observed that all three factors were necessary and sufficient to transform lumens bordered by tubule cells possessing a polarized epithelial cell phenotype with extensive microvili-formation and tight junctional complexes along the lumenal border. RA promoted the deposition of the A and B1 chains of laminin, a cell attachment protein on the basement membrane in a small sub-set of proximal tubule cells and culture, as confirmed by indirect immunofluorescent microscopy. This confirmed a coordinated interplay between growth factors and retinoids to induce pattern formation and morphogenesis. Retinoic acid appeared to be essential for development of tubule epithelial cell polarity and lumen formation which is disrupted in PKD.

It is also noted that laminin production is changed at different periods of cyst development in PKD as reviewed by (Calvet, *Kidney Int.,* 43:101–108 (1993)). Retinoic acid has been shown to increase laminin production in embryonal cell lines by promoting laminin gene transcription (65,66, 67). Humes et al., supra. postulated the critical roles in tubulogenesis increased renal tubular cell adhesion and aggregation due to TGF-beta 1, stimulation of renal cell proliferation with EGF and induction of tubular cell polarization with RA. It is suggested that cells which respond to retinoic acid with laminin deposition are indeed the renal tubule stem cells capable of replication and terminal phenotiypic differentiation.

Further effects of retinoids during vertebrate development are reviewed by Ragsdale et al., *Current Opinion in Cell Biol.,* 3(6): 928–934 (1991). Retinoids are required for vertebrate development and can act as teratogens partly due to their ability to cause cells to drop out of differentiation and division. They intervene in pattern formation at a strategic level as seen in their affect on polarization in chick limb-bud formation action. At low doses, the main effect of retinoic acid is felt to be on patterning with complete block of growth and mitotic inhibition at high doses. There are alpha, beta and gamma forms of retinoic acid receptors in the human, mouse and rat genomes as reviewed by Mattei et al., in *Genomics,* 10:1061–1069 (1991).

Growth factors are polypeptides which stimulate a wide variety of biological responses (e.g., DNA synthesis, cell division, expression of specific genes, etc.) in a defined population of target cells. A variety of growth factors have been identified, including the transforming growth factor family of polypeptides—epidermal growth factor (EGF), platelet-derived growth factor (PDGF), fibroblast growth factor (FGF), insulin-like growth factors (IGF-I and IGF-II).

IGF-I and IGF-II are polypeptides with each molecule having a molecular weight of approximately 7500 daltons. IGF-II is believed to play a major role in fetal growth. In contrast, IGF-I acts as the mediator of the effects of growth hormone (GH) and thus is the primary mediator of growth after birth. IGF-I has also been implicated in the actions of various other growth factors, since treatment of cells with such growth factors leads to increased production of IGF-I. Both IGF-I and IGF-II have insulin-like activities, as indicated by the chosen name of the peptide, and are mitogenic for the cells in reproductive tissue, muscle, skeletal tissue and a wide variety of other tissues. IGF-I and IGF-II were originally name somatomedins, indicative of their growth promoting and mitogenic effects.

Unlike most other growth factors, the IGFs are present in substantial quantity in the circulation, but only a very small fraction of IGF is found in free form in the circulation or in other body fluids. The overwhelming majority of IGF circulates as part of a non-covalently associated ternary complex composed of IGF-I or IGF-II, and IGF specific binding protein termed IGFBP-3, and a large protein termed the acid labile subunit (ALS). This complex is composed of equimolar amounts of each of the three components. The ALS has no direct IGF binding activity and is thought to only be able to bind a preformed IGF-I/IGFBP-3 complex. The ternary complex of IGF+IGFBP-3+ALS has a molecular weight of approximately 150,000 daltons, and it has been suggested that the function of such a unit in the circulation is as a reservoir and a buffer for IGF-I and IGF-II, theeby preventing rapid changes of free IGF.

Nearly all of the IGF-I or IGF-II and IGFBP-3 in the circulation are complexed with each other, so there is very little free IGF or IGFBP-3 detectable.

IGF-I may be purified from natural sources or produced from recombinant sources. For instance, IGF-I has been purified from human serum for a number of years. See Rinderknecht, et al., *Proc. Natl. Acad. Sci. U.S.A.,* 73(7): 2365–2369 (1976). Recombinant IGF-I processes are shown in EPA 0,128,733, published in December of 1984.

IGF-I may be measured in blood serum to diagnose abnormal growth-related conditions, e.g. pituitary gigantism, acromegaly, dwarfism, various growth hormone deficiencies, etc. Although IGF-I is produced in many tissues, most circulating IGF-I is believed to be synthesized in the liver.

Example 1
IGF-I Administration in cpk Mice

A total of 17 litters from known cpk heterozygote paired matings were enrolled in IGF treatment at 24 hours of age. This yielded a total of 23 proven cpk homozygotes confirmed by palpation of cystic kidneys in the second week of life and also by pathological assessment at death. The animals received 0.05 mg (0.01 ml=0.05 mg) of IGF-I injected on postnatal day 2 until postnatal day 7 and 0.1 mg (0.02 ml=0.1 mg) injected subcutaneously from postnatal day 8 to postnatal day 25. The litters were separated between postnatal day 20 and 25 and all animals were killed on postnatal day 45.

A control group consisting of 45 cpk/cpk mice received 0.01 ml of saline on postnatal day 2 to postnatal day 7 and 0.02 ml of saline on postnatal day 8 to postnatal day 25. Weaning also occurred in this group between postnatal day 20 and 26.

All animals were killed on postnatal day 45 with the exception of one cystic mouse in the IGF treatment group who had palpable large cystic kidneys and was allowed to live beyond the closure of the study group and died at 79 days of age with a weight of 10.58 grams, left kidney weight of 1 gram, and right kidney weight of 0.87 grams.

All mice were weighed daily and animals who died prior to the closure of the study had weights recorded at death along with tissue taken with appropriate weights of the left kidney, right kidney and liver. The tissues were fixed in 10% formulin and processed for histological assessment. All animals completing 45 days in each treatment arm were sacrificed with recording of their weight, respective kidney weights, and liver weight. The kidneys and liver were put in 10% formulin for histological assessment. Blood was also taken from each animal.

Kaplan-Meier survival curves were constructed to graphically compare the IGF-I and control groups. The relative odds of survival (see Mantel N: Evaluation of survival data and two new rank order statistics arising in its consideration. *Can Chemo Reports* 50:163–170, (1966)) and the relative risk of death (see Gill R., Schumacher M.: A simple test of the proportional hazards assumption. *Biometrika* 74:289–300, (1987)) were used as summary statistics. The proportional hazards assumption was tested using the Gill-Schumaker test (see Gill supra). The hypothesis of homogeneity of survival functions was tested using a log-rank test (Mantel-Cox) and a rank-sum test (Peto-Prentice). In comparing survival between two groups using a log-rank or rank-sum test, no change in the test statistic or significance level occurs after the death of the last subject in one of the groups, day 45 in this case. Therefore, longevity in one or two mice in the IGF-I treatment group makes no difference to the statistical inference. The kidney weight, the total body weight, and the anephric body weight (carcass weight minus kidney weight) were used as independent variables in analyses of covariance, with the independent variable being an indicator variable for the absence or presence of IGF-I, and the concomitant variable being the time of death (which was also the age at measurement). The ratio of the total kidney weight to the anephric body weight was used as an index or surrogate assessment of the amount of cystic disease at death. This ratio was used as a dependent variable in a regression analysis with the dependent variables being time of death and an indicator variable for the presence or absence of IGF-I treatment. The usual test for homogeneity of slopes, the usual lack-of-fit test for ordinary linear models and tests for absence of quadratic components were used to test the aptness of the model. A Bartlett-Box test showed homogeneity of variances between the different levels of the independent variable. The Komolgorof-Schmiernof/Lillifores test was used to demonstrate normality at these same levels.

cpk homozygotes receiving IGF-I from postnatal day 2 to 25 survived significantly longer than the saline-injected cpk control mice, as shown in FIG. 1. Mantel-Cox log-rank test produced a $\chi^2$ statistic of 19.727 and Peto-Prentice rank-sum test gave a $\chi^2$ statistic of 14.361. Both tests, with one degree of freedom, gave a P value of <0.00001. The Gill-Schumaker test demonstrated consistency with proportional hazards ($\chi^2$=0.123, 1 df, p=0.725). Hence, the statistical assessment showed enhanced survival of cpk homozygotes receiving IGF-I. There was no change in survival of the presumed heterozygote and normal litter mates, with the majority of the animals completing the 45 days of the study. One cpk mouse receiving IGF-I lived 79 days of age, while the longest survivor in the control group lived only 29 days.

Figure 4:
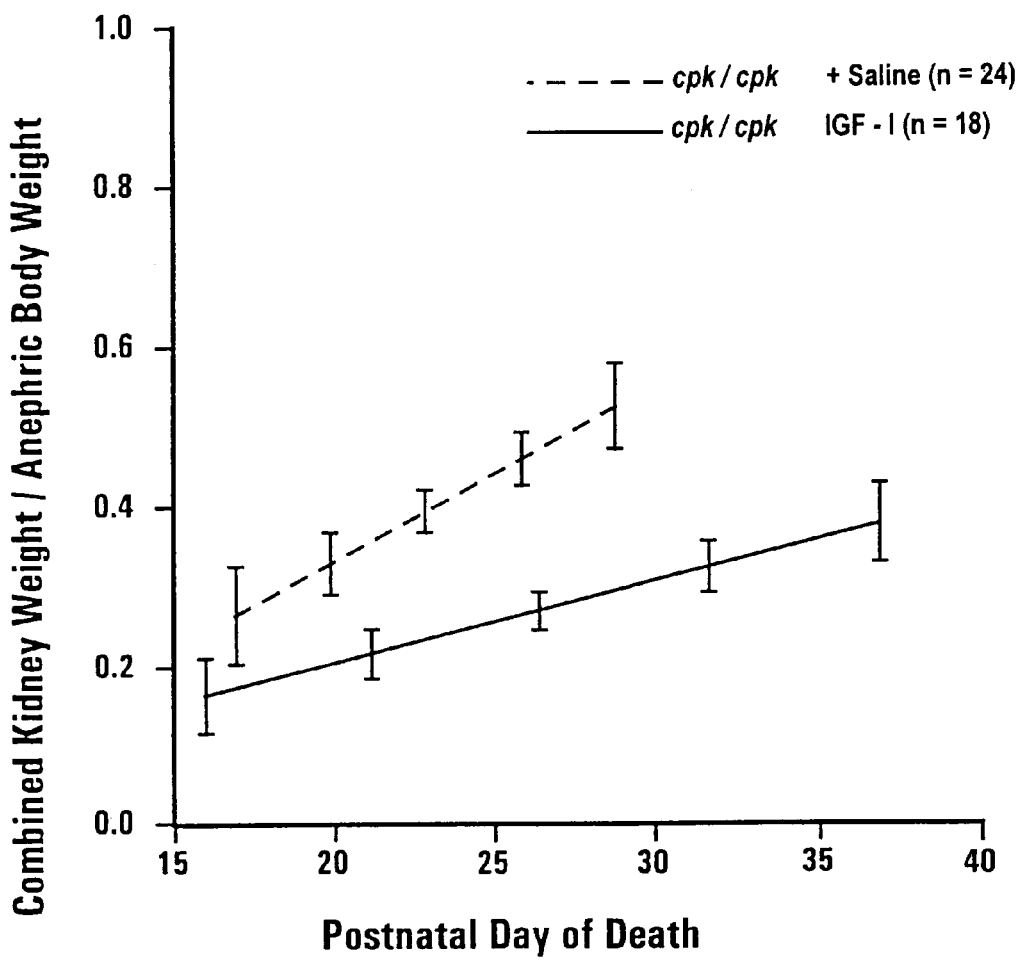
FIG. 4 illustrates the influence of IGF-1 on the ratio of kidney weight to anephric body weight at the time of death in the cpk/cpk model. The vertical error-bars on the fitted lines are standard errors of the estimate at 5 equally spaced times of death. The horizontal projection of each line on the abscissa gives the range of times of death for each experiment.

In the genetic model, the degree of cyst formation at the time of death was extensive in both the IGF-I treated and saline treated homozygotes on gross examination, although the kidneys of the IGF-I treated mice appeared smaller. Microscopic examination revealed that in the saline group, preserved organized renal tissue was almost non-existent, but in the IGF-I group there were islands of renal tissue with nearly normal structure. The mean kidney weight (g), adjusted for age at death, for the IGF-I group (1.635±0.149, n=18), compared with the saline group (2.106±0.1294, n=24) was significantly smaller ($F_{1,39}$=5.450, p=0.025). The total body weight (g), adjusted for age at death, of the IGF-I treated mice (8.281±0.284), compared with saline treated mice (7.003±0.244), was significantly increased ($F_{1,39}$=11.164, p=0.002). Furthermore, the mean anephric body weight (g), adjusted for age of death, of the IGF-I group (6.646±0.207) compared with the saline group (4.897±0.178) was also significantly increased ($F_{1,39}$=39.1890, p=0.000). The kidney weight to anephric weight ratio had an acceptable linear relationship with age of death over the course of the experiment (FIG. 4) (lack-of-fit $F_{13,9}$=0.939, p=0.509 for IGF-I and $F_{1,06}$=1.095, p=0.428 for saline; combined quadratic component $F_{1,38}$=3.594, p=0.066). There was no significant treatment-time interaction ($F_{1,38}$=1.499, p=0.228), indicating that the condition of parallel slopes was also acceptable over the range of the experiment. The kidney weight to anephric weight ratio was, on average, 17.3% smaller in the IGF-I treated group, compared with the saline treated group ($F_{1,34}$=20.648, p=0.000). Since the adjusted mean kidney weight was smaller in the IGF-I treated group, and the total and anephric body weights were larger, it has clearly been demonstrated that the separation of lines of the kidney to anephric body weight ratio over time reflects decrease in cystic disease by IGF-I in the cpk/cpk neonatal genetic model of PKD. The mean liver weight (g) for the IGF-I group (0.297±0.018, n=17), compared to the saline group (0.237±0.015, n=24), was significantly larger ($F_{1,39}$=6.274, p=0.017). Adjustments for body weight, anephric body weight or time of death made no difference. In consideration of these results and the results for body weight, it is clearly shown that IGF-I promotes anabolic growth and solid organ growth.

cpk/cpk homozygotes receiving IGF-I from postnatal day 2 to 25 survived significantly longer than cpk/cpk control mice. Indeed, some animals lived more than double the average life expectancy (with one cpk/cpk mouse receiving IGF-I living until 79 days of age), with control mice living a maximum of 29 days. There was no change in survival of the presumed heterozygote and normal litter mates, with the majority of animals completing the 45 day study. The degree of cyst formation at the time of death was extensive in both the IGF-I treated and saline treated animals. Microscopic assessment revealed that in the saline group, preserved organized renal tissue was almost non-existent, but in the IGF-I group there were islands of renal tissue with nearly normal structure. The mean kidney weight (g), adjusted for age at death, for the IGF-I group (1.635±0.149, n=18) compared with the saline group (2.106±0.1294, n=24) was significantly smaller ($F_{1,39}$=5.450, p=0.025). The total body weight (g), adjusted for age at death, of the IGF-I treated mice (8.281±0.284), compared with saline treated mice (7.003±0.244), was significantly increased ($F_{1,39}$=11.164, p=0.0018). Furthermore, the mean anephric body weight (g), adjusted for age of death, of the IGF-I group (6.646±0.207), compared with the saline group (4.897±0.178), was also significantly increased ($F_{1,39}$=39.1890, p<0.0001). The kidney weight to anephric weight ratio was, on average, 17.3% smaller in the IGF-I treated group compared with the saline treated group ($F_{1,34}$=20.648, p=0.000). Since the adjusted mean kidney weight was smaller in the IGF-I treated group, and the total and anephric body weights were larger, it has clearly been demonstrated that the separation of lines of the kidney to anephric body weight ratio over time reflects decrease in cystic disease by IGF-I in the cpk/cpk neonatal genetic model of PKD. The mean liver weight (g) for the IGF-I group (0.297±0.018, n=17), compared to the saline group (0.237 ±0.015, n=24), was significantly larger ($F_{1,39}$= 6.274, p=0.017). In consideration of these results and the results for body weight, it has also clearly been demonstrated that IGF-I promotes anabolic growth and solid organ growth.

Example 2
IGF Treatment in Glucocorticoid-Induced PKD

The role of IGF-I in the GIPKD model was addressed. A total of 149 C57BL/6J newborn mice were entered into the study at 24 hours of age after suckling was established with the mothers. They were divided into 4 groups:

A) control (n=34);
B) IGF-I, 50 mg/kg/dose subcutaneously q12hx8 doses starting at 24 hours of age (n=41);
C) Methylprednisolone acetate (MPA) 250 mg/kg intramuscularly at 24 hours of age (n=72); and
D) Methylprednisolone acetate 250 (MPA) mg/kg intramuscularly at 24 hours of age, plus IGF-I, 50 mg/kg/dose subcutaneously q12hx8 doses starting at 24 hours of age (n=49).

Each litter had daily weights obtained of each mouse. All animals were killed at 120 hours of age (postnatal day 6). Glucose determination was done with glucometer Elite. Kidneys and livers were harvested and processed for valuation of the pathological scale of cystic disease. Blood was pooled from each litter for subsequent analysis.

Figure 5:
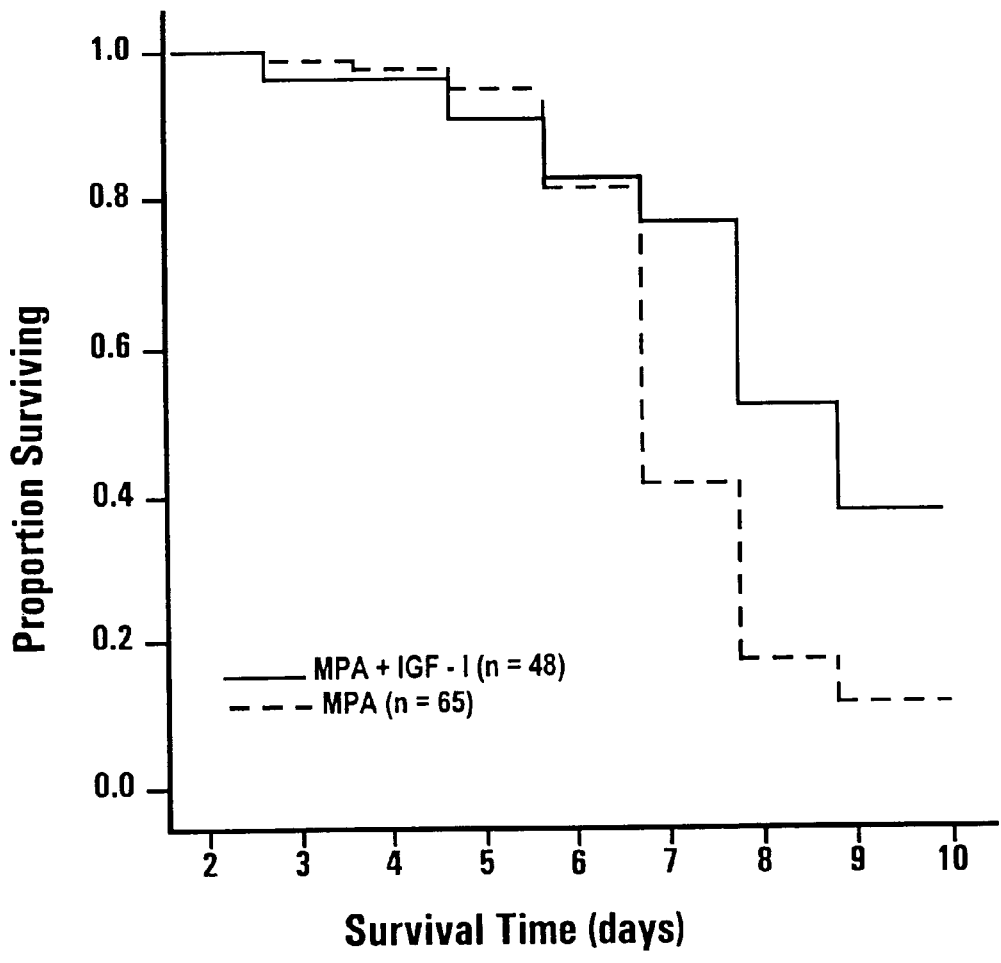
FIG. 5 presents plots of Kaplan-Meier survival estimates for the GIPKD_model with and without IGF-I. The plots demonstrate increased survival for mice given IGF-I for 9 days.

Kaplan-Meier survival curves were constructed to compare the MPA and MPA+IGF-I treatment groups (see FIG. 5). Summary statistics were calculated and tests for the proportional hazards assumption and for homogeneity of survival functions were done as in the genetic model.

Comparison of cystic disease incidence between the MPA and MPA+IGF-I treated groups, the only groups demonstrating cystic disease, was done using a Fisher exact test (2 tailed). Comparisons of the distribution of disease severity was done with a model comparison approach in multinominal ordinal regression response models using a probit link (see Cox C: Location-scale cumulative odds ratio for ordinal data. A generalized non-linear model approach. *Stat in Med* 14:1191–1203 (1995), and Angelos Tosteson A N, Begg C B: A general regression methodology for ROC curve estimation. *J Royal Stat Soc* (Series B) 42:109–142 (1980)). Difference in overall body weight gain was assessed using the Tukey-Kramer method of pairwise comparisons of means. Pairwise comparisons of the mean glucose concentrations were done using separate-variance estimates of error terms since homoscedasticity could not be achieved using simple transformations.

All parameter estimates in both models are reported with ±standard error. Within families of tests, reported p-values are corrected for simultaneous inference using a Holmes procedure (see Wright S P: Adjusted p-values for simultaneous inference. *Biometrics* 48:1005–1013 (1992)) or Tukey-Kramer procedure. However, throughout these experiments, at a family-wise type-1 error rate of 0.05, the statistical inference for the corrected p-values was exactly the same as without the correction.

Figure 2:
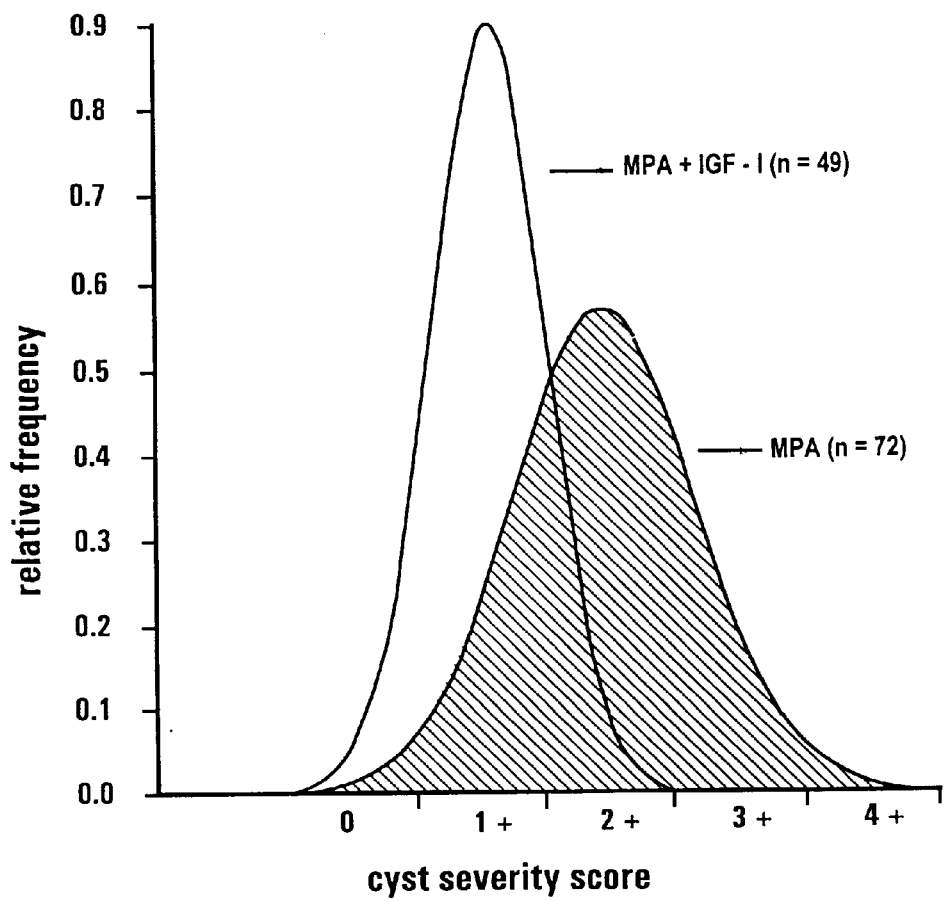
FIG. 2 presents normal distributions fitted to cyst severity, illustrating the reduction of cyst severity achieved upon treatment of GIPKD mice with IGF-I. The left shift of the mean from 1.454 to 0.564 upon treatment with IGF-I is statistically significant (Deviance=44.177, 1 df, p<0.00001). The variance was also reduced from 0.703 to 0.444 (Deviance=1.420, 1 df, p<0.0064).
Figure 3A:
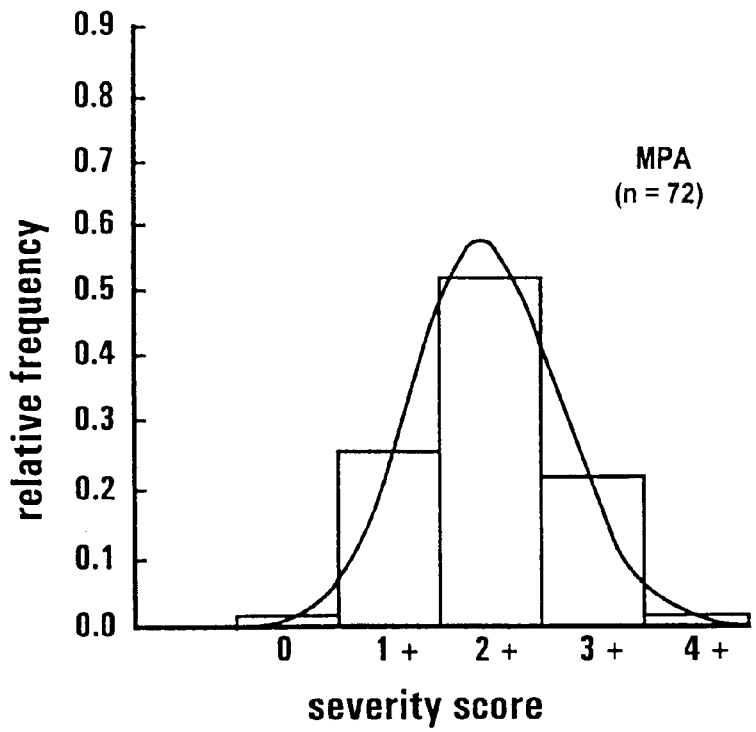
FIG. 3A presents results with MPA treated mice.
Figure 3B:
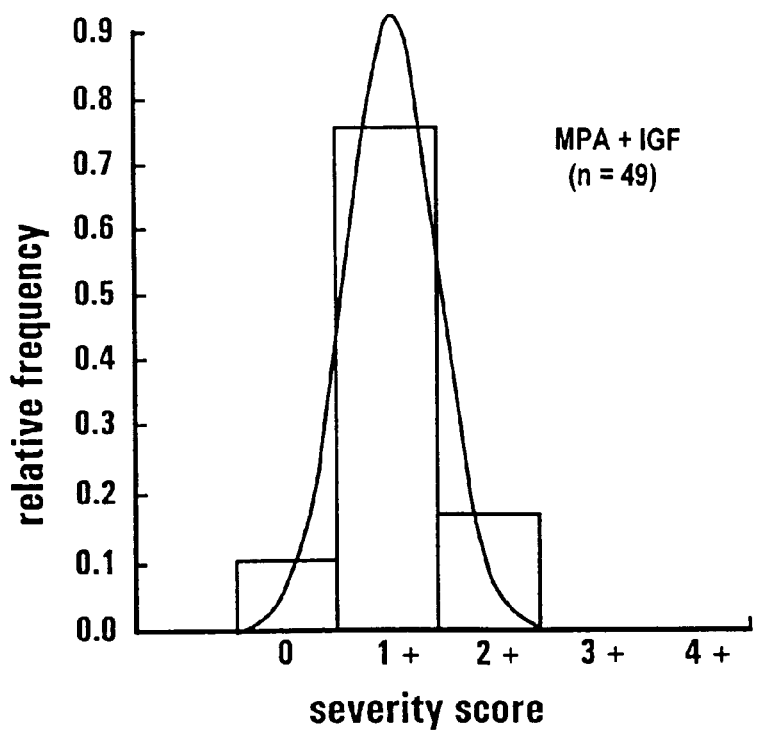
FIG. 3B presents results with MPA+IGF-I treated mice. The likelihood ratio goodness-of-fit statistic for the combined estimation was $\chi^2=0.225$, 2 df, p=0.894. In the IGF-I-treated group, the mean is shifted to the left (Deviance=44.177, 1 df, p=0.00001) so that the proportion of affected mice is less and the degree of severity is less, with a smaller variance (Deviance=7.420, 1 df, p<0.0064).

IGF-I showed significant reduction of cyst severity of GIPKD with complete protection of some animals (see FIGS. 2 and 3). The severity of cyst score fitted a normal distribution for both the MPA and MPA+IGF-I treatment groups. The addition of IGF-I resulted in a shift to the left (i.e., cyst reduction) of the mean cyst score from 1.454 to 0.564, which is statistically significant (Deviance=44.177, 1 df, p<0.00001) . The variance was also reduced from 0.703 to 0.444 (Deviance=1.420, 1 df, p<0.0064). IGF-I significantly reduced the glucocorticoid-induced hyperglycemia seen in MPA-treated neonates. The third major finding was the reduction of the glucocorticoid-induced catabolism and weight loss. The control group, IGF-I, and MPA+IGF-I group showed no difference in weight gain and were statistically different than the MPA treated group alone.

In the GIPKD model, the addition of IGF-I to MPA results in a significant decrease in the incidence of cystic disease from 98.6% to 88.9% (Fisher exact test p=0.031). The severity of cyst scores fitted a normal distribution for both the MPA and MPA+IGF-I treatment groups (goodness-of-fit $\chi^2$=0.225, 2 df, p=0.894). The addition of IGF-I results in a shift to the left with a significant decrease in the mean score from 1.454 to 0.564 (compare FIGS. 3A and 3B) (Deviance (D) $\chi^2$=44.177, 1 df, p=0.000). There is also a statistically significant decrease in variance from 0.703 to 0.444 (D=7.420, 1 df, p=0.006). This may be spurious and reflect the relatively coarse measurement of cystic disease severity. These results clearly demonstrate that IGF-I reduces cystic disease incidence and severity in this GIPKD model.

There was also observed to be an improvement of the poor weight gain secondary to glucocorticoid-induced catabolism in the IGF-I treated group of the GIPKD model. Pairwise comparisons (Tukey-Kramer) of the 5 day average weight (g) gain per mouse for the control litters (1.583±0.086, n=6 litters) and IGF-I litters (1.357±0.080, n=7 litters) were not statistically different (p=0.248). Similarly, the average weight (g) gain per mouse for IGF-I litters and the MPA+IGF-I litters (1.075±0.105, n=4 litters) was not different (p=0.177), although control was different from MPA+IGF-I (p=0.007). However, the weight gain per mouse of the MPA litters (0.583g (0.086, n=6 litters) was significantly smaller than the other groups (all three p<0.010). For this experiment, these multiple pairwise comparisons infer a ranking of the total weight gain: Control≧IGF-I≧MPA+IGF-I>MPA. These experiments clearly demonstrate that IGF-I reverses the negative glucocorticoid effect on weight gain in the immediate postnatal period.

The mean glucose concentration (mmol/l) in the MPA treated group (26.33±1.79, n=36) was observed to be markedly higher than that of controls (5.84±0.12, n=34) ($F_{1,35.3}$=130.471, p=0.000). The addition of IGF-I to the MPA treatment reduced the concentration (to 13.234±0.932, n=38). This is still significantly larger than that of the control group ($F_{1,38.3}$=61.815, p=0.000), but is significantly smaller than that of the MPA group ($F_{1,52.9}$=42.124, p=0.000). The concentration for the group which received IGF-I alone was 5.604±0.093 (n=41), and this was not statistically different from the control group ($F_{1,64.1}$=2.359, p=0.130).

IGF-I showed significant reduction of cyst incidence and severity in the GIPKD model, with complete protection of some animals. IGF-I significantly reduced the glucocorticoid-induced hyperglycemia and hypokalemia seen in MPA treated neonates. In addition, IGF-I reduces glucocorticoid-induced catabolism and weight loss. The control group, IGF-I, and MPA+IGF-I group showed no difference in weight gain; this profile was statistically different than the poor weight gain of the MPA treated group. The IGF-I+MPA treated animals had lower creatinine (see Table 1), urea (see Table 1), and uric acid levels than MPA treated animals on P6.

TABLE 1

Biochemical data of pooled litter serum samples from GIPKD model killed on postnatal day 6 (Least squared means +/− standard errors)

| Treatment[a] | No. of litters[b] | creatinine (mcmole/l) | urea (mmole/l) |
|---|---|---|---|
| P6 control | 15 (97) | 34.26 ± 15.41 | 9.45 ± 2.40 |
| MPA on P2 (MPA) | 17 (107) | 89.35 ± 14.47 | 36.76 ± 2.32 |
| IGF-I 50 mg/kg/dose bid sc on P2–P5 (IGF-I × 8) | 8 (57) | 51.25 ± 21.10 | 8.79 ± 3.28 |
| MPA + IGF-I bid on P2–P5 (MPA + IGF-I × 8) | 7 (45) | 70.71 ± 22.56 | 18.50 ± 3.51 |
| IGF-I on P2 (IGF-I × 1) | 5 (36) | 36.70 ± 26.69 | 11.85 ± 4.64 |
| MPA + IGF-I (MPA + IGF-I × 1) | 3 (22) | 63.67 ± 34.46 | 19.00 ± 5.36 |

[a]All MPA administrations employed 250 mg/kg
All IGF-I administrations employed 50 mg/kg
[b]The total number of animals tested is designated in parenthesis This study confirms that:

1) IGF-I causes significant reduction of severity and incidence of glucocorticoid-induced renal cystic disease,
2) IGF-I has biological activity when given subcutaneously to neonatal animals with increased doses tolerated in the first week of life,
3) IGF-I decreased the glucocorticoid-induced hyperglycemia in neonatal animals, and
4) IGF-I protects the catabolic effects of high-dose corticoticoids on growth in neonatal mice.

The extensive nature of the testing conducted in support of the work described herein is clear upon inspection of the data summarized in Table 2.

TABLE 2

Summary of Biochemical Data from Pooled Litter Samples Evaluating the Presence or Absence of Renal Insufficiency

| | P6 Control | MPA (GIPKD) | IGF-1 X8 doses | IGF-1 X8 doses + MPA | IGF-1 X1 dose | IGF-1 X1 dose + MPA |
|---|---|---|---|---|---|---|
| Normal Renal Function (Creatinine < 65 μmol/L) | 15 litters (n = 97) | 8 litters (n = 57) | 7 litters (n = 50) | 5 litters (n - 34) | 5 litters (n = 36) | 2 litters (n = 18) |
| Deterioration of Renal Function (renal insufficiency/failure) (Creatinine > 65 μmlo/L) | 0 litters (n = 0) | 9 litters (n = 50) | 1 litter (n = 2) | 2 litters (n = 11) | 0 litters (n = 0) | 1 litter (n = 4) |
| Total @ Risk | 15 litters (n = 97) | 17 litters (n = 107) | 8 litters (n = 52) | 7 litters (n = 45) | 5 litters (n = 36) | 3 litters (n = 22) |

IGF-I has also been shown to reduce mortality in the GIPKD model similar to the cpk/cpk model. Mice receiving MPA 250 mg/kg im at 24 hours of age have >80% mortality within 10 days of age, with significant evidence of catabolism and poor weight gain. All treated mice die by 13 days of age. In the group which received IGF-I in addition to MPA, there was a significant increase in growth and a reduction of mortality to less than 40% at 10 days. Survival analysis confirms that IGF-I decreases mortality in the GIPKD model. The surviving mice with IGF-I treatment on P10 did have evidence of renal failure, with urea and creatinine levels comparable to P6 MPA treated animals. IGF-I appeared to delay, but not eliminate, renal failure in the GIPKD model.

It has also been shown herein that giving only one dose of IGF-I to the GIPKD model at the time of the MPA administered on postnatal day 2 gives similar results to the twice daily administered IGF-I animals. These results show that a single dose of IGF-I, given at the same time as a toxic amount of steroid, can indeed improve renal failure, decrease cystic disease, reduce steroid induced hyperglycemia, reverse and/or augment the catabolic effects of steroids (supported by reduction of urea and improved growth with IGF-I treatment), and improve somatic growth in mammals.

Example 3

IGF-I in GIPKD (Survival Study)

A total of 177 C57BL/6J newborn mice were entered into a study at 24 hours of age after suckling was established with the mothers. They were divided into 2 treatment groups:

A) Methylprednisolone acetate (MPA) 250 mg/kg intramuscularly at 24 hours of age (n=123) and
B) Methylprednisolone acetate (MPA) 250 mg/kg intramuscularly at 24 hours of age, plus IGF-I 50 mg/kg/dose q12h starting at 24 hours of age until death or 10 days postnatal (n=54).

During the course of the experiments, the litters were weighed daily and any deaths were recorded with harvesting of kidneys and liver where appropriate. The kidneys were subsequently assessed for pathological scale of cystic disease. At the end of 10 days, all remaining mice who had not died were sacrificed. The purpose of this study arm was to address whether IGF would reduce mortality in the GIPKD model.

In the group of mice receiving methylprednisolone acetate at 24 hours of age, there was an 88% mortality within 10 days of age (i.e., 108 of 123 died), with significant evidence of catabolism and poor weight gain. In the group receiving IGF-I in addition to methylprednisolone acetate, there was a significant increase in growth and a reduction of mortality at 10 days of age to 66% (i.e., 36 of 54 died). Survival analysis confirms that IGF-I decreases mortality in the GIPKD model.

The three studies summarized in Examples 1, 2 and 3 above document that IGF-I ameliorates renal cystic disease in both the cpk/cpk mutant mouse and GIPKD. Mortality was decreased in both models, and IGF-I was seen to have a positive effect on somatic growth. In addition, there was a reduction of hyperglycemia noted in the GIPKD model. The results presented herein also support the theory that IGF-I given subcutaneously to neonates can have biological effect and that this group of animals tolerate higher doses than mature animals. Neonatal mice used in a steroid-induced gastrointestinal villous atrophy model required higher doses of IGF-I, compared with older animals. This may be explained by the relative increase of insulin growth factor binding protein-I and the KD 40 complex seen in the fetal and newborn period, which is effective in delivering IGF-I to the glomerular ultrafiltrate.

IGF-I may be the most important polypeptide growth factor in cystic disease in the pathogenesis of cystic disease as a common end point. This is supported by the fact that the dominant kidney tubule production is confined to the collecting tubule, where most cysts are observed, with no apparent production in other segments of the tubule. In contrast, epidermal growth factor is synthesized in the thick ascending look of Henle. There is evidence of increased secretion of EGF in cystic fluid whereas EGF administered to cpk mice enhances survival. Cystogenesis promoted by EGF is a compensatory mechanism with overproduction whereas it is more likely that IGF-I is a decrease of synthesis in paracrine function. Also, it is noted that EGF decreases glomerular filtration whereas IGF-I increases glomerular filtration. The differences between these two different growth factors are important and may provide some insight into the role of growth factors in the evolution of cystic disease.

The role of IGF-I in decreasing hyperglycemia without inducing hypoglycemia in the GIPKD model emphasizes that the administered dose is absorbed and this effect is most likely through its action on the glucose transporter mechanism.

The enhancement of growth in both models support the conclusion that IGF-I is a useful therapeutic modality in the treatment of neonatal growth failure induced by glucocorticoids and also in uremic induced growth failure.

In conclusion, it has been shown that IGF-I ameliorates renal cystic disease in both the genetic cpk mutant model and in GIPKD in C57BL/6J mice. This result provides insight into the pathway of cystic action within kidney. It has also been shown that IGF-I can be administered to neonatal animals, with the benefit of IGF-I in neonatal growth being explicitly demonstrated. It has further been shown that IGF-I can be added to epidermal growth factor as a second growth factor that is beneficial in the treatment of cystic disease.

While the invention has been described in detail with reference to certain preferred embodiments thereof, it will be understood that modifications and variations are within the spirit and scope of that which is described and claimed.

That which is claimed is:

1. A method for the treatment of polycystic kidney disease in a mammal, said method comprising administering to a mammal in need thereof an amount of IGF-I effective to substantially reduce kidney cyst incidence and/or severity.

2. A method according to claim 1 wherein said polycystic kidney disease is the result of genetic predisposition.

3. A method according to claim 2 wherein said polycystic kidney disease is transmitted as an autosomal dominant trait.

4. A method according to claim 2 wherein said polycystic kidney disease is transmitted as an autosomal recessive trait.

5. A method according to claim 1 wherein said polycystic kidney disease is the result of a spontaneous genetic mutation.

6. A method according to claim 1 wherein said polycystic kidney disease is acquired as a result of exposure to environmental factors.

7. A method according to claim 6 wherein said polycystic kidney disease is acquired in response to treatment with agents which affect metanephric development.

8. A method according to claim 7 wherein said agent which affects metanephric development is a steroid hormone.

9. A method according to claim 8 wherein said steroid hormone is a glucocorticoid.

10. A method for the treatment of polycystic kidney disease in a mammal, said method comprising administering to a non-adult mammal in need thereof an amount of free IGF-I effective to substantially reduce kidney cyst incidence and/or severity, wherein said polycystic kidney disease is acquired in response to treatment with teratogenic agents.

11. A method according to claim 10 wherein said teratogenic agent is an amine or a plasticizer.

12. A method according to claim 11 wherein said amine is diphenylamine.

13. A method according to claim 11 wherein said plasticizer is a phthalate.

14. A method according to claim 1 wherein said mammal is human.

15. A method according to claim 1 wherein said IGF-I is human IGF-I.

16. A method according to claim 1 wherein said IGF-I is mature, native human IGF-I.

17. A method according to claim 1 wherein said IGF-I is an IGF-I analog, homolog or mimic.

18. A method according to claim 1 wherein said IGF-I is an IGF-I analog wherein the glutamic acid at position 3 is deleted or replaced by another amino acid residue.

19. A method according to claim 1 wherein said IGF-I is formulated in a pharmaceutically acceptable carrier.

20. A method according to claim 1 wherein said IGF-I is formulated in sterile, isotonic medium.

21. A method according to claim 1 wherein said IGF-I is administered by continuous infusion.

22. A method according to claim 1 wherein said IGF-I is administered parenterally.

23. A method to enhance glomerular development in a mammal, said method comprising administering an effective amount of free IGF-I to a mammal in need thereof.

24. A method to enhance kidney development in a mammal suffering from chronic organ injury, said method comprising administering an effective amount of free IGF-I to said mammal.

* * * * *